United States Patent [19]

Fuchs

[11] 3,987,096

[45] Oct. 19, 1976

[54] PROCESS FOR CHLORINATION OF ACETALDOXIME

[75] Inventor: Julius Jakob Fuchs, Wilmington, Del.

[73] Assignee: E. I. Du Pont de Nemours and Company, Wilmington, Del.

[22] Filed: Jan. 20, 1975

[21] Appl. No.: 542,608

[52] U.S. Cl. .............................................. 260/566 A
[51] Int. Cl.² ..................................... C07C 131/00
[58] Field of Search ................................ 260/566 A

[56] References Cited
UNITED STATES PATENTS

| | | | |
|---|---|---|---|
| 3,574,736 | 4/1971 | Fuchs............................ | 260/566 A |
| 3,658,869 | 4/1972 | Soloway......................... | 260/566 A |
| 3,752,841 | 8/1973 | Fuchs............................ | 260/566 A |

Primary Examiner—Gerald A. Schwartz

[57] ABSTRACT

Continuous or semi-continuous process for preparing acetohydroxamyl chloride. Acetaldoxime and chlorine are introduced simultaneously into an aqueous reaction medium. The reaction is conducted at an acetaldoxime concentration below 1%.

6 Claims, 2 Drawing Figures

PROCESS FOR CHLORINATION OF ACETALDOXIME

BACKGROUND

This invention relates to the discovery of side reactions contributing to yield loss in the chlorination of acetaldoxime in aqueous solution and the development of an improved process that obviates these side reactions and consequently increases yield. This clorination releases a large heat of reaction, 57.5 kilocalories per mole of oxime, and generates HCl. Yield loss is apparently caused by side reactions such as hydrolysis of acetaldoxime and acetohydroxamyl chloride by the acidic solution. The side reactions are rapidly accelerated at high temperatures.

U.S. Pat. No. 3,574,736, issued to J. J. Fuchs, teaches the chlorination of acetaldoxime in aqueous solution using a batch process in which all of the oxime is charged first to a reactor and then chlorine is gradually added. Batch chlorination yields are 10–15% lower than those of continuous chlorination most likely because of hydrolysis of acetaldoxime in acid medium. In addition, the control of temperature rise from the very high heat of reaction is somewhat difficult in a batch process. This control is important for at temperatures above 10° C yield loss evidently due to hydrolysis of the product, acetohydroxamyl chloride, can also be significant.

U.S. Pat. No. 3,658,869, issued to Soloway, discloses a process for chlorination of acetaldoxime by either batch or continuous operation. The continuous operation uses a packed column in which the oxime flows downward, countercurrent to chlorine fed up through the column, and a cooling jacket is used to remove heat of reaction. The composition of the reaction medium varies through the column from aqueous oxime to finished product. Oxime concentration would be as high as 7.5% in the upper part of the reactor, and, therefore, the oxime is quite susceptible to acid hydrolysis. This process method is not advantageous for commercial use. To provide sufficient heat transfer for commercial production rates it would be necessary to provide a multiplicity of jacketed packed tubes. Such equipment would be expensive and difficult to operate. If a larger diameter jacketed column were used, heat transfer would be inefficient and part of the reaction mass would be subjected to high temperatures where hydrolysis is rapid.

As recognized by those skilled in the art, excess chlorine will ordinarily result in overchlorination and production of undesired 1,1,1-dichloronitrosoethane and similarly a deficiency of chlorine will result in underchlorination and the unreacted oxime will represent a yield loss. No accurate and reliable method for preventing such chlorination problems is furnished by prior art processes.

SUMMARY

According to this invention there is provided an improved process for the continuous or semi-continuous chlorination of acetaldoxime to produce acetohydroxamyl chloride. Acetaldoxime and chlorine are introduced simultaneously into an aqueous reaction medium and the reaction is conducted at an acetaldoxime concentration of less than 1% of the reaction mass by weight.

The process of this invention constitutes an improvement over previous processes for the chlorination of acetaldoxime. Yields based on acetaldoxime are generally in the range of 80–85% for batch processes. Yields can be improved by about 10–15% using this invention. The acetaldoxime concentration is always maintained below 1% and preferably below 0.3%. At these low values, yield loss due to acetaldoxime hydrolysis is minimized. Also, the large heat of reaction generated by the main reaction is absorbed by the large reaction mass so that the temperature may be controlled easily in a commercial scale reactor. Low temperatures reduce the yield loss due to product hydrolysis and lend great flexibility to the operation of a commercial unit with respect to temperature and residence time. In addition, oxidation-reduction potential measurements provide a convenient and reliable method to insure stoichiometric equivalence between acetaldoxime and chlorine. Complete reaction can be accomplished, the concentration of unreacted oxime kept low and the unwanted side reaction caused by addition of another chlorine to form 1,1,1-dichloronitrosoethane is minimized.

A preferred process involves the continuous operation depicted in FIG. 2. The reaction is conducted in a closed loop reactor in which the reaction medium, containing about 5–18% acetohydroxamylchloride and about 2–9% HCl is circulated at high volume flow rate within the reactor. Acetaldoxime and chlorine are introduced simultaneously and continuously at different points in the reactor. The feed rates of these two reactants are adjusted so that the acetaldoxime concentration is kept below 1% by weight of the reaction mass at the point where chlorine is introduced. This continuous procedure is particularly advantageous: heat removal is uniform, mixing of reactants is efficient, and the degree of reaction is conveniently controlled by instrumentation.

DETAILED DESCRIPTION

Figure 1:
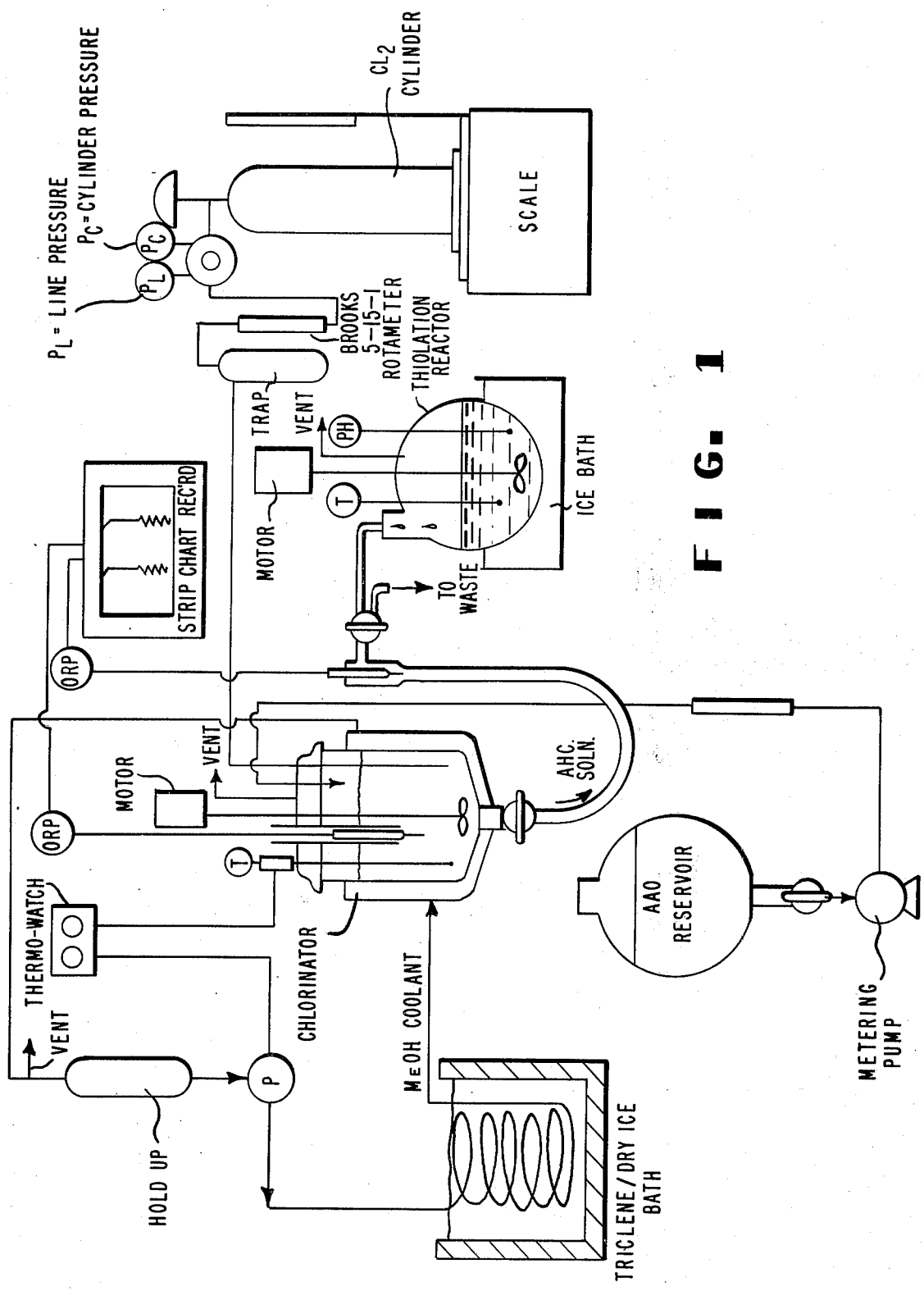

The process is characterized by (1) the use of water or acetohydroxamyl chloride and HCl in water as liquid reaction medium (2) the controlled addition of acetaldoxime to keep the concentration at very low levels to minimize hydrolysis losses, (3) the control of temperature rise due to a very high heat of reaction by a large dilution of reactants in the liquid medium, and (4) the control of stoichiometry of reactants by measurements of oxidation-reduction potential of the reacting solutions.

The chemistry of the chlorination is illustrated by the following formulas:

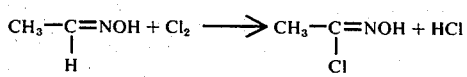

The continuous process includes these operational steps: (1) A liquid reaction medium consisting of aceto-hydroxamyl chloride, HCl, and water is circulated at a high volume flow rate within a closed loop reactor. The liquid reaction medium can contain about 5–18% by weight acetohydroxyamyl chloride, about 2–9% by weight HCl, and the remainder water. A concentration of 16–18% acetohydroxamyl chloride and 8–9% HCl is preferred. (2) An aqueous solution of acetaldoxime is added at a constant rate to the stream of liquid reaction medium. The acetaldoxime is added at a feed rate that produces a concentration of less than 1% by weight of the reaction mass at the point where chlorine is introduced. A concentration of 0.2% by weight of acetaldoxime is preferred. (3) The acetaldoxime is thoroughly mixed with the liquid reaction medium. (4) Chlorine gas or liquid is added continuously at a rate that is stoichiometric to the addition rate of acetaldoxime. (5) The liquid reaction medium containing the reacting acetaldoxime and chlorine, is then passed through a heat exchanger to remove the heat of reaction. The effluent stream from the heat exchanger is returned to a ballast tank.

Product is continuously withdrawn from the recirculating reaction mass at a point remote from the acetaldoxime and chlorine feeds, at a rate that maintains the reactor contents at a constant volume. The product stream, which composition remains constant, is then suitable for its intended use. The acetohydroxamyl chloride is suitable for direct reaction with a sodium mercaptide to produce the thiohydroxamate ester, which is an intermediate in the production of insecticides.

To minimize decomposition of acetohydroxamyl chloride and acetaldoxime the liquid reaction medium should be maintained between −15° C and 20° C. A temperature range of 0° C to 10° C is preferred. The combined feed rates of acetaldoxime and chlorine are maintained at a value that will keep the acetohydroxamyl chloride residence time between ½ and 8 hours. A convenient and reliable method to monitor and control these flow rates is to feed acetaldoxime at a desired steady rate and control the addition of chlorine by oxidation-reduction potential (ORP) measurements. The difference in the ORP (ΔORP) monitored at the point of entry of chlorine and the point just before the return of the stream to the ballast tank can be used to indicate the degree of reaction. In general, the ΔORP desired is between 150 and 350 millivolts. A ΔORP of about 250 millivolts is preferred.

It is preferable to run the reaction so that the acetohydroxamyl chloride and HCl concentrations are respectively 16% and 8%, the temperature between 0° C and 10° C, and the holding time approximately 1 hour. The acetaldoxime concentration in the reaction medium at the point of addition will be about 0.3% under these conditions. The ΔORP is maintained at about 250 millivolts.

In the semi-continuous method acetaldoxime and chlorine are fed into either water or an aliquot of the reaction mixture from a previous batch. The chlorinated acetaldoxime and water accumulate until a batch is finished and then product is transferred to the succeeding reaction step. The essential characteristics are the same as the continuous operation. Acetaldoxime and chlorine are fed simultaneously with good mixing in the reactor in such a way that the acetaldoxime concentration is always kept very low, below 1%, and the temperature is controlled by dilution of the reactants in the reaction medium coupled with heat removal by jacket cooling or cooling by an external heat exchanger. The concentration of acetohydroxamyl chloride is kept below 18% and the temperature is kept below 20° C.

At temperatures between 0° C and 10° C the major source of yield loss in the chlorination of acetaldoxime is due to acid catalyzed hydrolysis of acetaldoxime to form the aldehyde and hydroxylamine.

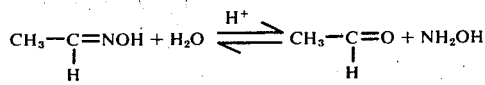

Yield loss due to this reaction is reduced as the acetaldoxime concentration is reduced.

At temperatures above 10° C yield loss due to hydrolysis of the product, acetohydroxamyl chloride, can be significant.

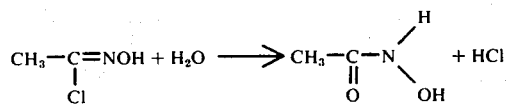

At 10° C the residence time must be less than 1 hour; at 20° C the residence time must be less than 30 minutes, or yield losses due to product hydrolysis will render the process impractical.

The following Examples further illustrate the invention. Parts and percentages in these Examples are by weight unless otherwise specified.

EXAMPLE 1

A 1 liter, jacketed resin kettle along with the associated equipment is shown in FIG. 1.

A 13% acetaldoxime solution at 16 grams per minute was fed into a rapidly stirred solution of 16% acetohydroxamyl chloride and 8% HCl in water. Gaseous chlorine was added at such a rate as to maintain the oxidation-reduction potential difference between the two probes shown at about 250 millivolts. The temperature was controlled at 0° ± 2° C by means of coolant MeOH (methanol) circulated through the reactor jacket. The residence time was approximately ¾ hour.

Effluent was withdrawn at the same rate as the combined input and fed into 178.5 g of an aqueous solution containing 29.2% potassium methyl mercaptide and 18.7% potassium hydroxide. The temperature was kept at 25° C and the addition stopped when the pH was 7. Twenty percent of the weight of the product slurry was distilled at 50° C and 100 mm Hg pressure. The slurry was then exhaustively extracted with methylene chloride. The extract was dried, and stripped. The product, S-methyl-N-hydroxythioacetimidate, was recovered in 91.6% yield with a melting point of 90°–92° C.

EXAMPLE 2

A 52.1% aqueous solution of acetaldoxime and gaseous chlorine were fed into 200 g of water at 0° C. The feed rates were adjusted to maintain the oxidation-reduction potential of the solution near the endpoint of the reaction. This insured an oxime concentration less than 1%. The temperature was maintained at 0° C. The pot volume increased until a total of 56.6 g of 52.1% oxime solution and 35.5 g of chlorine had been added. The product solution was converted to S-methyl-N-hydroxythioacetimidate as in Example 1. 46.1 g of product were recovered. The yield based on acetaldoxime was 87.8% and the melting point was 91°–93° C.

EXAMPLE 3

Figure 2:
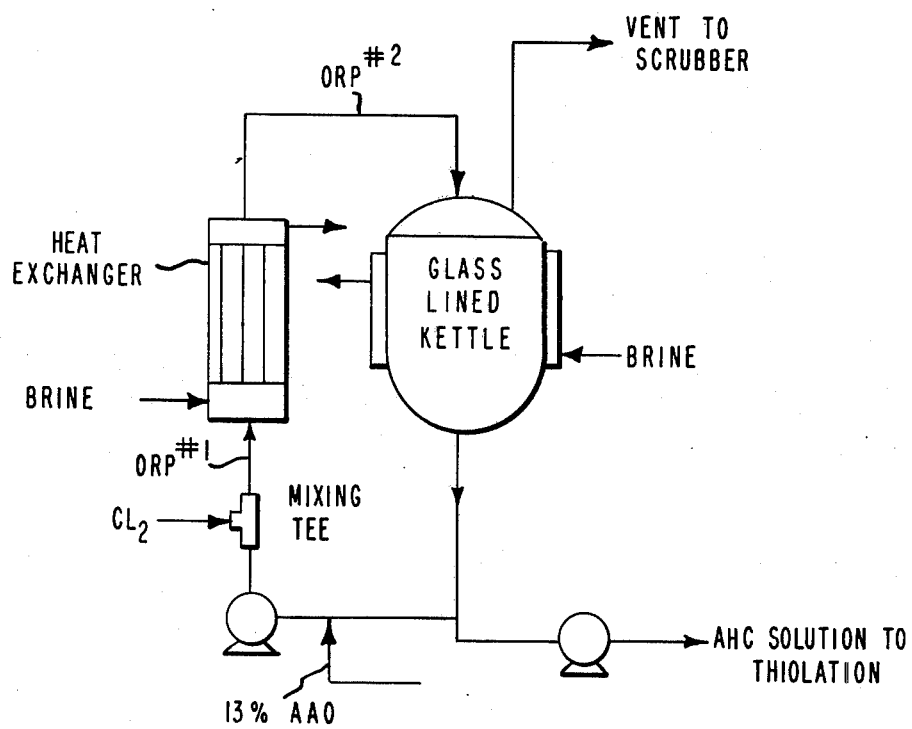

A schematic of a continuous commercial chlorinator is shown in FIG. 2. A large centrifugal pump circulates a total of 250 parts of an aqueous solution of 16% acetohydroxyamyl chloride and 8% HCl at the rate of 500 parts per minute in a loop through a heat exchanger and expansion vessel. A 13% by weight aqueous solution of acetaldoxime is fed to the suction side of the pump at the rate of 8.9 parts per minute. Liquid chlorine is injected on the discharge side of the pump in such a manner as to insure good mixing with the reaction mass. The heat of reaction is removed in the heat exchanger and the reaction temperature is controlled at 0° ± 2° C. The chlorine feed rate is controlled so that the difference in oxidation-reduction potential between the two designated points (ORP No. 1 and ORP No. 2) is about 250 millivolts. Product is removed from the bottom of the reaction vessel continuously, at a rate of 10.3 parts per minute. The expected yield of acetohydroxamyl chloride based on methylthio acetaldoxime is approximately 92%.

I claim:

1. In the process for preparing acetohydroxamyl chloride of the formula

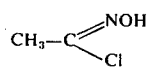

by reaction of acetaldoxime and chlorine in an aqueous reaction medium, the improvement which comprises introducing the reactants simultaneously into the reaction medium in a manner that maintains the concentration of acetaldoxime below 1% by weight of the reaction mass.

2. The process of claim 1 in which oxidation-reduction potential measurements are used to monitor stoichiometric equivalence of the reactants.

3. The process of claim 1 which comprises:
   1. conducting the reaction in a closed loop reactor in which the reaction medium containing about 5–18% acetohydroxamoyl chloride and about 2–9% HCl is circulated at high volume flow rate within the reactor;
   2. introducing the reactants continuously into the circulating reaction medium.

4. The process of claim 3 in which oxidation-reduction potential measurements are used to monitor stoichiometric equivalence of the reactants.

5. The process of claim 3 in which the aqueous reaction medium comprises 16–18% acetohydroxamoyl chloride and 8–9% HCl.

6. The process of claim 3 in which the concentration of acetaldoxime is below 0.3%.

* * * * *